United States Patent
Jiang et al.

(10) Patent No.: US 10,759,827 B2
(45) Date of Patent: Sep. 1, 2020

(54) METHOD FOR SEPARATING AND PURIFYING MOGROSIDE V BY SUBCRITICAL WATER DESORPTION TECHNOLOGY

(71) Applicant: GUILIN LAYN NATURAL INGREDIENTS CORP., Guilin (CN)

(72) Inventors: Minglian Jiang, Guilin (CN); Wenguo Yang, Guilin (CN); Yunfei Song, Guilin (CN); Yuanyuan Li, Guilin (CN)

(73) Assignee: Guilin Layn Natural Ingredients Corp., Guilin (CN)

( * ) Notice: Subject to any disclaimer, the term of this patent is extended or adjusted under 35 U.S.C. 154(b) by 0 days.

(21) Appl. No.: 16/156,976

(22) Filed: Oct. 10, 2018

(65) Prior Publication Data

US 2019/0040097 A1    Feb. 7, 2019

Related U.S. Application Data

(63) Continuation of application No. PCT/CN2017/080813, filed on Apr. 17, 2017.

(30) Foreign Application Priority Data

Mar. 14, 2017  (CN) .......................... 2017 1 0151350

(51) Int. Cl.
    *C07J 17/00* (2006.01)
    *A23L 27/30* (2016.01)

(52) U.S. Cl.
    CPC ............. *C07J 17/005* (2013.01); *A23L 27/33* (2016.08); *A23V 2002/00* (2013.01)

(58) Field of Classification Search
    None
    See application file for complete search history.

(56) References Cited

U.S. PATENT DOCUMENTS

| | | | |
|---|---|---|---|
| 6,124,442 A | 9/2000 | Zhou et al. | |
| 2016/0031778 A1* | 2/2016 | Garikipati | B01D 3/143 435/158 |

FOREIGN PATENT DOCUMENTS

| | | | | |
|---|---|---|---|---|
| CN | 101177444 A | * | 5/2008 | ............. A23L 27/30 |
| CN | 101336987 A | * | 1/2009 | ........... A61K 36/752 |
| CN | 101690573 | | 4/2010 | |
| CN | 102408320 A | * | 4/2012 | ........... C07C 49/255 |
| CN | 102408463 | | 4/2012 | |
| CN | 103923152 | | 7/2014 | |
| CN | 103980335 | | 8/2014 | |

OTHER PUBLICATIONS

Xia, Y., Rivero-Huguet, M. E., Hughes, B. H., & Marshall, W. D. (2008). Isolation of the sweet components from Siraitia grosvenorii. Food Chemistry, 107(3), 1022-1028. (Year: 2008).*

* cited by examiner

*Primary Examiner* — Dale R Miller
(74) *Attorney, Agent, or Firm* — Levine Bagade Han LLP

(57) ABSTRACT

The invention relates to a method for separating and purifying mogroside V by subcritical water desorption technology. The macroporous adsorption resin enriched with mogroside V is subjected to desorption under a subcritical condition of water using water as a solvent, to give an aqueous solution rich in mogroside V. The method not only improves the content of mogroside V in product, but also effectively removes bitter impurities and residual pesticides, greatly improves the taste adaptability of the product, and improves the safety and quality of the product. The method reduces the processing steps and reduces the use of organic solvents in the prior art, and reduces total production costs.

6 Claims, No Drawings

METHOD FOR SEPARATING AND PURIFYING MOGROSIDE V BY SUBCRITICAL WATER DESORPTION TECHNOLOGY

CROSS-REFERENCE TO RELATED APPLICATIONS

This application is a continuation of International Application No. PCT/CN2017/080813, filed Apr. 17, 2017, which claims priority to Chinese Application No. 201710151350.1, filed Mar. 14, 2017, both of which are incorporated by reference in their entireties.

TECHNICAL FIELD

The present invention relates to a method for separating and purifying mogroside V, in particular, to a method for separating and purifying mogroside V by subcritical water desorption technology.

BACKGROUND ART

Mogroside V, also known as momordica-glycosides, is the main sweet component of *Siraitia grosvenori* of Genus *Siraitia* in Cucurbitaceae. Its sweetness is 350 times of sucrose. At present, seven monomer components have been identified, among which, mogroside V and Siamenoside I have the highest sweetness. Mogroside has the characteristics of low sugar, low calorie and the like, has the improvement effects to the immune system, liver and blood glucose of the modern consumers, and can meet the health requirements of contemporary consumers. Compared with the traditional natural sweetener stevioside, mogroside V has a mouthfeel closer to sucrose, no bitter taste, which can make up for the deficiencies of stevioside to some extent.

With the continuous increasing of the quantity demanded and quality requirement of mogroside V in the market, especially the more stringent requirements for improvement of mouthfeel and reduction of pesticide residues, the task of improving the mouthfeel and quality of mogroside V is extremely urgent. However, the compositions of the *Siraitia grosvenori* extract are complex, which increase the difficulty of separating and purifying mogroside V in the preparation process. In addition, the low content of mogroside V in natural *Siraitia grosvenori* results in high production cost of mogroside V, which cannot meet the demand of mass marketization of mogroside V.

In the prior art, mogroside V is separated and purified mainly by the following processes: adsorbing and enriching mogroside V by ion exchange resin and macroporous adsorption resin, adding deionized water or purified water to wash the column so as to remove residual impurities and partial pigments; and then adding organic solvent such as ethanol so as to desorb the mogroside V from the macroporous adsorption resin, thereby obtaining mogroside V. For example, Reference Document 1 (Chinese Patent Application Publication No. CN101177444A) discloses "a method for extracting mogroside from *Siraitia grosvenori*", wherein the steps of extraction, ultrafiltration, concentration, enrichment of mogroside by macroporous adsorption resin, washing with purified water, elution with ethanol, and recovery of ethanol are performed in order to give a *Siraitia grosvenori* extract containing mogroside. The products obtained by ethanol desorption have low content of mogroside and comprise many bitter impurities, which greatly affect the mouthfeel, and the ability to remove residual pesticides of this method cannot meet the increasingly stringent quality requirements. The tedious elution step and the recovery of ethanol also increase the time and cost of the whole production process.

In order to make up for the deficiency of macroporous resin adsorption-ethanol elution technology, it is needed to refine and purify *Siraitia grosvenori* extract by using a variety of resins or materials having different properties in the prior art. For example, Reference Document 2 (Chinese Patent Publication No. CN101690573B) discloses "a method for producing a *Siraitia grosvenori* extract with a content of mogroside V of 60% or more", in which the *Siraitia grosvenori* is subjected to crush, saccharification, extraction, concentration, centrifugation, refinement with ion exchange resin, enrichment with macroporous adsorption resin, desorption with ethanol, recovery of ethanol, and refinement with alumina column so as to give a *Siraitia grosvenori* extract containing mogroside. Although the method can make up for a part of deficiencies of ethanol elution, the process steps of refinement with ion exchange resin and refinement with alumina column are increased, which may increase the total production cost and be not conducive to large-scale production.

In subcritical water extraction, water is used as the extraction solvent, and it still remains in liquid state when heated to 100 to 374° C. under an appropriate pressure, but the physical and chemical properties thereof are greatly different from those of water at normal temperature and pressure. When the temperature is low, water molecules are close to each other, while under subcritical state, with the elevation of the temperature, the kinetic energy of molecules increases, the intermolecular distance becomes larger, and the fluid microstructure including hydrogen bonding, ion hydration and ion association, cluster structure and the like all change. Therefore, by controlling the temperature and pressure of the subcritical water, the polarity of water is changed within a large range, so that target components with different polarity can be continuously separated and extracted from the mixture. There is no report on the application of subcritical water technology for the desorption from macroporous resins.

SUMMARY OF THE INVENTION

In order to overcome the deficiencies in the prior art, the object of the present invention is to provide a method for separating and purifying mogroside V by subcritical water desorption technology. The method for separating and purifying mogroside V can increase the content of mogroside V in product, effectively remove bitter impurities and residual pesticides, greatly improve the mouthfeel adaptability of the product, and improve the safety and quality of the product. The method for separating and purifying mogroside V can reduce the process steps and the use of organic solvents, and decrease the total production cost compared with that in the prior art.

The purpose of the present invention can be achieved by the following technical solutions.

The present invention provides a method for separating and purifying mogroside V by subcritical water desorption technology, in which desorption-extraction is carried out on a macroporous adsorption resin enriched with mogroside V using purified water in a subcritical state, to give a *Siraitia grosvenori* aqueous solution.

Preferably, desorption-extraction is carried out on a macroporous adsorption resin enriched with mogroside V using 5 to 8 BV purified water in a subcritical state under a pressure of 8 to 15 Mpa and a temperature of 120 to 170° C. at a circulation velocity of 5 to 8 BV/h, to give a *Siraitia grosvenori* aqueous solution.

Preferably, desorption-extraction is carried out on a macroporous adsorption resin enriched with mogroside V using 5 BV purified water in a subcritical state under a pressure of 10 Mpa and a temperature of 160° C. at a circulation velocity of 5 BV/h, to give a *Siraitia grosvenori* aqueous solution.

Preferably, the obtained *Siraitia grosvenori* aqueous solution containing mogroside V is concentrated through ceramic membrane with a relative molecular weight cutoff of 150 to 250, to give a *Siraitia grosvenori* concentrated solution. When the ceramic membrane is used for concentration, the small molecular impurities can be filtered out while water is filtered out, so that the purification and concentration are carried out simultaneously, which further improves the production efficiency.

Preferably, the macroporous adsorption resin enriched with mogroside V is prepared by the following steps:

(1) the raw material of *Siraitia grosvenori* fresh fruit or dried fruit is crushed, and then extracted with purified water as solvent using a continuous dynamic countercurrent extraction apparatus under the following conditions: a solid-liquid ratio of 50 to 250 g/L, a temperature of 60 to 90° C., a circulation velocity of the purified water of 1,500 to 4,000 L/h, a raw material feeding rate of 500 to 1,500 kg/h, and a time period for extraction of 30 to 180 min, so as to give a water extract of *Siraitia grosvenori*;

(2) the water extract of *Siraitia grosvenori* obtained in step (1) is centrifuged at a rotation speed of 10,000 to 13,000 r/min for 10 to 20 min so as to give a centrifuged liquid;

(3) the centrifuged liquid obtained in step (2) is filtered successively through a ceramic membrane having a pore size of 50 to 100 μm and a ceramic membrane having a pore size of 5 to 20 μm, so as to give a filtrate; and (4) the filtrate obtained in step (3) is absorbed by macroporous adsorption resin with the mass ratio of the used macroporous adsorption resin to the raw material of *Siraitia grosvenori* being 1:5 to 1:20, so as to give a macroporous adsorption resin enriched with mogroside V.

Preferably, the macroporous adsorption resin enriched with mogroside V is prepared by the following steps:

(1) the raw material of *Siraitia grosvenori* fresh fruit or dried fruit is crushed, and then extracted with purified water as solvent using a continuous dynamic countercurrent extraction apparatus under the following conditions: a solid-liquid ratio of 90 g/L, a temperature of 85° C., a circulation velocity of the purified water of 2,500 L/h, a raw material feeding rate of 1,100 kg/h, and a time period for extraction of 120 min, so as to give a water extract of *Siraitia grosvenori*;

(2) the water extract of *Siraitia grosvenori* obtained in step (1) is centrifuged at a rotation speed of 12,000 r/min for 15 min so as to give a centrifuged liquid;

(3) the centrifuged liquid obtained in step (2) is filtered successively through a ceramic membrane having a pore size of 80 μm and a ceramic membrane having a pore size of 10 μm, so as to give a filtrate; and (4) the filtrate obtained in step (3) is absorbed by macroporous adsorption resin with the mass ratio of the used macroporous adsorption resin to the raw material of *Siraitia grosvenori* being 1:10, so as to give a macroporous adsorption resin enriched with mogroside V.

Preferably, the macroporous adsorption resin in step (4) is a microspheric macroporous adsorption resin.

In the present invention, the subcritical conditions of water suitable for dissolving out mogroside V is investigated and determined, so that the mogroside V component adsorbed on the macroporous resin can be maximally transferred to the subcritical water fluid, thereby improving the desorption efficiency. Subcritical water extraction has the advantages of high recovery rate for target components, low requirements for equipment, high efficiency and time saving. Compared with the methods using organic solvent as an extraction solvent, the present invention has the advantages of high safety, non-toxicity, environmental friendliness and the like, and solves the problem that the total production cost is excessively high due to the recovery of organic solvents.

The present invention also overcomes at least one of the following technical problems: when the macroporous adsorption resin enriched with mogroside V is under a subcritical state of water, the pore diameter of microparticles of the resin becomes larger due to the influence of the conditions of high temperature and high pressure, and parts of impurities (including residual pesticides) which are closely adsorbed on the macroporous resin at room temperature are released. At the same time, the macroporous resin will be melted and deformed due to high temperature and high pressure, which affects the separation and purification of mogroside V. Therefore, in order to ensure the effective desorption of mogroside V and to avoid the influence of unfavorable conditions such as dissolution of impurities (including residual pesticides) and resin melting, the selection of the conditions of appropriate temperature and pressure is one of the key problems to be solved by the present invention. Experiments carried out by the inventors show that, the macroporous resin will not melt and deform under the water subcritical state of a pressure of 8 to 15 MPa and a temperature of 120 to 170° C. At the same time, the results of the tests for various impurities (including residual pesticides) show that, under such conditions of pressure and temperature, the contents of various impurities (including residual pesticides) in the extract obtained by the desorption method according to the present invention are significantly less than those of the extract prepared by the prior art. When the pressure is 10 Mpa and the temperature is 160° C., the subcritical water has the greatest desorption effect on the mogroside V, and has the lowest dissolving capacity to other impurities. When the pressure is lower than 8 Mpa or higher than 15 Mpa, and the temperature is lower than 120° C. or higher than 170° C., the subcritical water has a certain desorption effect on the mogroside V, but at the same time it has a strong dissolving capacity to the impurity components, which is not conducive to the separation and purification of mogroside V.

The invention also provides a method for preparing mogroside V, characterized in that, mogroside V is prepared by drying the *Siraitia grosvenori* aqueous solution or *Siraitia grosvenori* concentrated solution prepared by the above method.

Compared with the prior art, the present invention has at least one of the following advantages:

1. In the mogroside V-containing product separated and purified by subcritical water desorption technology, the percentage content of mogroside V is higher than that of the prior art.

2. In the mogroside V-containing product separated and purified by subcritical water desorption technology, various pesticide residue indicators are significantly reduced compared with the prior art, which effectively improves the overall safety and quality of the product.

3. In the mogroside V-containing product separated and purified by subcritical water desorption technology, the indicators that reduce the mouthfeel pleasure, such as characteristic odor, characteristic taste, raw taste, bitterness, astringency, duration of sweet aftertaste, duration of bitter aftertaste, duration of astringent aftertaste, characteristic aftertaste and overall consistency, are all improved to some extent, the sweetness is increased, and the general mouthfeel pleasure is improved.

4. When the mogroside V is separated and purified by subcritical water desorption technology, the process steps are replaced or reduced, including removal of residual impurities and partial pigments by water elution after absorption-enrichment with macroporous resin, removal of residual pesticides by treatment with a residual pesticide-removing resin, improvement of mouthfeel by treatment with decolorizing resin, ion exchange resin and activated carbon; the production efficiency is improved, and the total production cost is reduced, which is conducive to the mass marketization of the product.

5. When the mogroside V is separated and purified by subcritical water desorption technology, the use of organic solvents such as ethanol is replaced or reduced, the cost for recovering organic solvents is reduced, the pollution to the environment is reduced, and the safety performance of the product is improved.

SPECIFIC MODES FOR CARRYING OUT THE EMBODIMENTS

The following Examples are intended to illustrate the present invention, but are not intended to limit the scope of the present invention.

Example 1

(1) 1,000 kg of *Siraitia grosvenori* dried fruits were crushed, and then extracted by continuous dynamic countercurrent extraction apparatus with purified water as solvent under the following conditions: a solid-liquid ratio of 50 g/L, a temperature of 90° C., a circulation velocity of purified water of 4,000 L/h, a raw material feeding rate of 1,500 kg/h, and a time period for extraction of 180 min, so as to give a water extract of *Siraitia grosvenori*;

(2) the water extract of *Siraitia grosvenori* obtained in step (1) was centrifuged at a rotation speed of 10,000 r/min for 20 min so as to give a centrifuged liquid;

(3) the centrifuged liquid obtained in step (2) was filtered successively through a ceramic membrane having a pore size of 50 μm and a ceramic membrane having a pore size of 5 μm so as to give a filtrate;

(4) the filtrate obtained in step (3) was absorbed by macroporous adsorption resin D101 with the mass ratio of the employed macroporous adsorption resin to the raw material of *Siraitia grosvenori* being 1:5, so as to give a macroporous adsorption resin enriched with mogroside V;

(5) desorption-extraction was carried out on the macroporous adsorption resin enriched with mogroside V using 8 BV purified water in a subcritical state under a pressure of 15 Mpa and a temperature of 170° C. at a circulation velocity of 8 BV/h, to give a *Siraitia grosvenori* aqueous solution; and (6) the *Siraitia grosvenori* aqueous solution obtained in step (5) was concentrated through a ceramic membrane with a relative molecular weight cutoff of 150, to give a *Siraitia grosvenori* concentrated solution.

Example 2

(1) 1,000 kg of *Siraitia grosvenori* dried fruits were crushed, and then extracted using a continuous dynamic countercurrent extraction apparatus with purified water as solvent under the following conditions: a solid-liquid ratio of 90 g/L, a temperature of 85° C., a circulation velocity of purified water of 2,500 L/h, a raw material feeding rate of 1,100 kg/h, and a time period for extraction of 120 min, so as to give a water extract of *Siraitia grosvenori*;

(2) the water extract of *Siraitia grosvenori* obtained in step (1) was centrifuged at a rotation speed of 12,000 r/min for 15 min so as to give a centrifuged liquid;

(3) the centrifuged liquid obtained in step (2) was filtered successively through a ceramic membrane having a pore size of 80 μm and a ceramic membrane having a pore size of 10 μm so as to give a filtrate;

(4) the filtrate obtained in step (3) was absorbed by microspheric macroporous adsorption resin with the mass ratio of the microspheric macroporous adsorption resin to the raw material of *Siraitia grosvenori* being 1:10, so as to give a microspheric macroporous adsorption resin enriched with mogroside V;

(5) desorption-extraction was carried out on the microspheric macroporous adsorption resin enriched with mogroside V using 5 BV purified water in a subcritical state under a pressure of 10 Mpa and a temperature of 160° C. at a circulation velocity of 5 BV/h, to give a *Siraitia grosvenori* aqueous solution; and (6) the *Siraitia grosvenori* aqueous solution obtained in step (5) was concentrated through a ceramic membrane with a relative molecular weight cutoff of 200, to give a *Siraitia grosvenori* concentrated solution.

Example 3

(1) 1,000 kg of *Siraitia grosvenori* dried fruits were crushed, and then extracted using a continuous dynamic countercurrent extraction apparatus with purified water as solvent under the following conditions: a solid-liquid ratio of 250 g/L, a temperature of 60° C., a circulation velocity of purified water of 1,500 L/h, a raw material feeding rate of 500 kg/h, and a time period for extraction of 30 min, so as to give a water extract of *Siraitia grosvenori*;

(2) the water extract of *Siraitia grosvenori* obtained in step (1) was centrifuged at a rotation speed of 13,000 r/min for 10 min so as to give a centrifuged liquid;

(3) the centrifuged liquid obtained in step (2) was filtered successively through a ceramic membrane having a pore size of 100 μm and a ceramic membrane having a pore size of 20 μm so as to give a filtrate;

(4) the filtrate obtained in step (3) was absorbed by macroporous adsorption resin D101 with the mass ratio of the macroporous adsorption resin to the raw material of *Siraitia grosvenori* being 1:20, so as to give a macroporous adsorption resin enriched with mogroside V;

(5) desorption-extraction was carried out on the macroporous adsorption resin enriched with mogroside V using 5 BV purified water in a subcritical state under a pressure of 8 Mpa and a temperature of 120° C. at a circulation velocity of 5 BV/h, to give a *Siraitia grosvenori* aqueous solution; and (6) the *Siraitia grosvenori* aqueous solution obtained in step (5) was concentrated through a ceramic membrane with a relative molecular weight cutoff of 250, to give a *Siraitia grosvenori* concentrated solution.

Comparative Example 1

This Comparative Example refers to the technical solution disclosed in the Reference document 1, and was used to evaluate the difference in technical effect between the technical solution of the Reference document 1 and that of the present invention. The specific steps were given as follows:

(1) 1,000 kg of fresh *Siraitia grosvenori* were fed together with water at a ratio of 1:15 into a countercurrent extraction apparatus in three equal portions at three time points with an interval of 20 min, and extracted at a temperature of 60° C. for 75 min;

(2) the extract solution was rough filtered and cooled to 40 to 50° C., and 0.5%0 of pectin complex enzyme was added to perform enzymolysis for 60 min.

(3) the extract solution undergoing enzymolysis was filtered through a 0.5 µm microfiltration membrane, rapidly cooled to 20° C., and centrifuged at 6,000 r/min, and then ultrafiltered with a hollow cellulose membrane with a relative molecular weight cutoff of 60,000 Daltons;

(4) the filtrate was concentrated to 6 Brix by vacuum concentrator at a temperature of 50 to 55° C. under a vacuum degree of 0.06 to 0.1;

(5) the concentrated solution was passed through macroporous adsorption resin D101 until a leak point was achieved, the effluent was discarded, and then the macroporous adsorption resin D101 was washed with deionized water;

(6) the macroporous adsorption resin D101 was eluted with 50% ethanol until it has no sweetness, and the ethanol eluate was collected;

(7) the ethanol eluate was decolorized with an anion exchange resin, and the decolorized solution was collected; and (8) ethanol was recovered from the decolorized solution, and the decolorized solution was concentrated in vacuum to give *Siraitia grosvenori* concentrated solution.

Comparative Example 2

The technical solution of this Comparative Example adopts subcritical water in an extraction step, and macroporous resin adsorption and water-ethanol elution in a desorption step, so as to evaluate the difference in technical effect between the technical solution in which the subcritical water was used for extraction and the technical solution of the present invention in which the subcritical water was sued for desorption from macroporous resin. The specific steps were given as follows:

(1) 1,000 kg of *Siraitia grosvenori* dried fruits were crushed, and then extracted using a continuous dynamic countercurrent extraction apparatus with purified water as solvent under the following conditions: a solid-liquid ratio of 90 g/L, a subcritical state with a temperature of 160° C. and a pressure of 10 Mpa, a circulation velocity of purified water of 2,500 L/h, a raw material feeding rate of 1,100 kg/h, and a time period for extraction of 120 min, so as to give a water extract of *Siraitia grosvenori*;

(2) the water extract of *Siraitia grosvenori* obtained in step (1) was centrifuged at a rotation speed of 12,000 r/min for 15 min so as to give a centrifuged liquid;

(3) the centrifuged liquid obtained in step (2) was filtered successively through a ceramic membrane having a pore size of 80 µm and a ceramic membrane having a pore size of 10 µm so as to give a filtrate;

(4) the filtrate obtained in step (3) was absorbed by microspheric macroporous adsorption resin with the mass ratio of the microspheric macroporous adsorption resin to the raw material of *Siraitia grosvenori* being 1:10, so as to give a microspheric macroporous adsorption resin enriched with mogroside V;

(5) the microspheric macroporous adsorption resin enriched with mogroside V was eluted with 5 BV purified water and 3 BV 50% (v/v) ethanol, the water eluate was discarded, and the ethanol eluate was collected;

(6) the ethanol was completely recovered and *Siraitia grosvenori* aqueous solution was obtained;

(7) the *Siraitia grosvenori* aqueous solution obtained in step (6) was successively passed through a residual pesticide-removing resin with a mass ratio to the raw material of *Siraitia grosvenori* being 1:100, a strongly acidic 001*1 resin with a mass ratio to the raw material of *Siraitia grosvenori* being 1:100, a decolorizing resin with a mass ratio to the raw material of *Siraitia grosvenori* being 1:40, and an activated carbon with a mass ratio to the raw material of *Siraitia grosvenori* being 1:10, to give a treated solution; and (8) the treated solution obtained in step (7) was concentrated through a ceramic membrane with a relative molecular weight cutoff of 200 to give *Siraitia grosvenori* concentrated solution.

Comparative Example 3

This Comparative Example refers to the technical solution disclosed in the Reference document 2, and was used to evaluate the difference in technical effect between the technical solution of the Reference document 2 and that of the present invention. The specific steps were as follows:

(1) 1,000 kg of fresh *Siraitia grosvenori* were taken and extracted for 3 times at a temperature of 90° C. or higher. The amount of water added was 5 times the weight of the raw material for the first extraction, 4 times the weight of the raw material for the second extraction and 3 times the weight of the raw material for the third extraction; and the extraction time was 1.5 h for the first extraction, 1.0 h for the second extraction and 0.5 h for the third extraction; after each extraction was completed, filtration was carried out, and filter residue was used as the raw material for the next extraction; the filtrates obtained from the three times of extraction were combined and concentrated under vacuum at a temperature of 75° C. or less to a weight 4 times the weight of the fed fruit;

(2) the concentrated extract solution was sedimentation-centrifuged at 2,000 to 4,000 r/min for 2 h;

(3) a resin column was loaded with strongly basic anion exchange resin D-201 which accounts for ¹⁄₁₀ of the weight of fresh *Siraitia grosvenori*, then the centrifugate was allowed to pass through the resin column, the effluent was collected, and the resin column was washed with purified water until it has no sweetness, and all effluents were combined;

(4) a resin column was pre-loaded with macroporous adsorption resin ADS-17 which accounts for 0.4 times of the weight of fresh *Siraitia grosvenori*, and the eluate treated with the ion exchange resin was passed through the resin column; and the resin column was washed with purified water until the effluent was colorless and transparent, finally, the resin column was desorbed with 55% edible ethanol, and the desorption solution was collected until it has no sweetness;

(5) the desorption solution was concentrated under vacuum-decompressed at a temperature of 75° C. or less to a weight of 0.5 times the weight of the fed *Siraitia grosvenori*;

(6) a resin column was pre-loaded with alumina which accounts for 0.04 times of the weight of fresh *Siraitia grosvenori*, the concentrated solution was diluted by 30 to 60 times, and passed through the alumina column, the effluent was collected, and the column was washed with purified water, and all effluents were collected; and (7) the effluent was concentrated under reduced pressure at a temperature of 75° C. or less to obtain a *Siraitia grosvenori* concentrated solution.

Detection Experiment for the Content of Mogroside V and Multiple Pesticide Residues 1. Instruments and Reagents Instruments: High Performance Liquid Chromatography (Agilent), Agilent 6495 Liquid series mass spectrometer LC-MS/MS, 0.45 μm microfiltration membrane and Syringe Filter, Pesticide Residue Purification Kit, microfiltration membrane 0.22 μm, oscillator, centrifuge, electronic balance (1/10,000), and ultrasonic cleaner.

Reagents: mogroside V standard substance (purchased from Chromadex), acetonitrile (chromatography grade), formic acid (mass spectrometry grade), ammonium formate (mass spectrometry grade), anhydrous magnesium sulfate (AR), sodium chloride (AR), methanol (AR), acetonitrile (chromatographically pure), and ultrapure water.

2. Method 2.1 Chromatographic Conditions and Operating Steps for the Determination of Mogroside V Chromatographic conditions: chromatographic column: LUNAC18, 250 mm×4.6 mm, 5 μm; mobile phase: acetonitrile (B)-0.1% phosphoric acid aqueous solution (A) being taken as mobile phase for gradient elution (0 to 17 min, 17→20%, phase B; 17 to 50 min, 20→26%, phase B), flow rate: 0.8 ml/min, detection wavelength: 203 nm; injection volume: 5 μl; and column temperature: 25° C.

Preparation of the test solution: about 60 mg (30%) of the sample was precisely weighed, placed in a 25 ml volumetric flask, dissolved by adding methanol, ultrasonically extracted for 15 min, cooled to room temperature, diluted with methanol to 25 mL, the mixture was shake up and passed through a 0.45 μm filter membrane.

Preparation of the standard solution: an appropriate amount of mogroside V standard substance was weighed precisely and prepared into a solution with a concentration of about 0.7 mg/ml by adding methanol. 5 μl of the standard substance solution and 5 μl of test solution were injected into the HPLC instrument respectively.

2.2 Chromatographic Conditions and Mass Spectrum Conditions for the Determination of Multiple Pesticide Residues Chromatographic conditions: chromatographic column: Agilent ZORBAX Eclipse Plus-C18 2.1 mm×100 mm, 1.8 μm; column temperature: 35° C.; needle washing: washing needle by needle seat with acetonitrile: water=10:90 for 3s; mobile phase: A: 0.1% formic acid and 0.1 mM ammonium formate aqueous solution, B: 0.1% formic acid in acetonitrile as mobile phase for gradient elution (0 to 10 min, 10→85%, phase B; 10 to 12 min, 85→95%, phase B), flow rate: 0.4 mL/min; stop time: 12 min; and post-run time: 3 min.

Conditions for mass spectrometry: Dry gas temperature: 250° C.; flow rate of dry gas: 11 L/min; pressure of atomization gas: 40 psi; capillary voltage: 3,500 V; sheath gas temperature: 350° C., and flow rate of sheath gas: 12 L/min.

3. Results 3.1 Effect of Different Processes on the Content Mogroside V in *Siraitia grosvenori* Concentrated Solution

TABLE 1

Effect of different processes on the content of mogroside V in *Siraitia grosvenori* concentrated solution

| Groups | mass fraction % of mogroside V |
|---|---|
| Example 1 | 59.26% ± 1.08% |
| Example 2 | 72.40% ± 1.26% |
| Example 3 | 55.07% ± 0.92% |
| Comparative Example 1 | 35.37% ± 2.15% |
| Comparative Example 2 | 42.18% ± 1.58% |
| Comparative Example 3 | 46.34% ± 1.74% |

3.2 Effect of Different Processes on the Residual Degree of Multiple Pesticides in *Siraitia grosvenori* Concentrated Solution

TABLE 2

Effect of different processes on the residual degree of multiple pesticides in *Siraitia grosvenori* concentrated solution

| Test items | Reporting threshold (mg/kg) | Example 1 | Example 2 | Example 3 | Comparative Example 1 | Comparative Example 2 | Comparative Example 3 |
|---|---|---|---|---|---|---|---|
| Acephate | 0.001 | less than reporting threshold | less than reporting threshold | less than reporting threshold | 0.1270 | less than reporting threshold | less than reporting threshold |
| Propamocarb | 0.001 | less than reporting threshold | less than reporting threshold | 0.0076 | 0.4053 | 0.0258 | 0.0863 |
| Carbendazim | 0.001 | 0.0276 | 0.0381 | 0.0952 | 4.6881 | 5.2012 | 3.2916 |
| Imidacloprid | 0.001 | 0.0015 | 0.0126 | 0.0098 | 2.8129 | 1.6251 | 1.2965 |
| acetamiprid | 0.001 | 0.0013 | less than reporting threshold | 0.0157 | 0.3437 | 0.1685 | 0.3817 |
| Tricyclazole | 0.001 | less than reporting threshold | less than reporting threshold | less than reporting threshold | less than reporting threshold | less than reporting threshold | less than reporting threshold |
| Oxadixyl | 0.001 | less than reporting threshold | less than reporting threshold | less than reporting threshold | less than reporting threshold | 0.1267 | 0.0985 |
| Thiophanate-methyl | 0.001 | less than reporting threshold | less than reporting threshold | less than reporting threshold | less than reporting threshold | less than reporting threshold | less than reporting threshold |

TABLE 2-continued

Effect of different processes on the residual degree of multiple pesticides in *Siraitia grosvenori* concentrated solution

| Test items | Reporting threshold (mg/kg) | Example 1 | Example 2 | Example 3 | Comparative Example 1 | Comparative Example 2 | Comparative Example 3 |
|---|---|---|---|---|---|---|---|
| Ametryn | 0.001 | less than reporting threshold | 0.0056 | 0.0126 | 0.7486 | 0.0514 | 0.0483 |
| Metalaxyl | 0.001 | 0.0018 | less than reporting threshold | 0.0282 | 0.4288 | 0.1592 | 0.0942 |
| Pyrimethanil | 0.001 | less than reporting threshold | less than reporting threshold | less than reporting threshold | 0.0082 | less than reporting threshold | less than reporting threshold |
| Isoprocarb | 0.001 | less than reporting threshold | less than reporting threshold | less than reporting threshold | less than reporting threshold | less than reporting threshold | less than reporting threshold |
| Triadimenol | 0.001 | less than reporting threshold | less than reporting threshold | less than reporting threshold | less than reporting threshold | less than reporting threshold | less than reporting threshold |
| Paclobutrazol | 0.001 | 0.0032 | less than reporting threshold | less than reporting threshold | 0.0572 | 0.1659 | 0.1365 |
| Dimethomorph | 0.001 | less than reporting threshold | less than reporting threshold | less than reporting threshold | less than reporting threshold | less than reporting threshold | less than reporting threshold |
| Methidathion | 0.001 | less than reporting threshold | less than reporting threshold | less than reporting threshold | less than reporting threshold | less than reporting threshold | less than reporting threshold |
| Diethofencarb | 0.001 | less than reporting threshold | less than reporting threshold | less than reporting threshold | less than reporting threshold | less than reporting threshold | less than reporting threshold |
| Myclobutanil | 0.001 | less than reporting threshold | less than reporting threshold | less than reporting threshold | less than reporting threshold | less than reporting threshold | less than reporting threshold |
| Iprovalicarb | 0.001 | less than reporting threshold | less than reporting threshold | less than reporting threshold | less than reporting threshold | less than reporting threshold | less than reporting threshold |
| Azoxystrobin | 0.001 | less than reporting threshold | less than reporting threshold | 0.0085 | 0.2652 | 0.0125 | 0.0688 |
| Triadimefon | 0.001 | 0.0018 | less than reporting threshold | less than reporting threshold | 0.0964 | 0.1351 | less than reporting threshold |
| Tebuconazole | 0.001 | less than reporting threshold | less than reporting threshold | less than reporting threshold | less than reporting threshold | less than reporting threshold | less than reporting threshold |
| Fluorosilazole | 0.001 | less than reporting threshold | less than reporting threshold | less than reporting threshold | less than reporting threshold | less than reporting threshold | less than reporting threshold |
| Hexaconazole | 0.001 | less than reporting threshold | less than reporting threshold | less than reporting threshold | 0.0284 | less than reporting threshold | less than reporting threshold |
| Metolachlor | 0.001 | less than reporting threshold | less than reporting threshold | less than reporting threshold | 0.0197 | less than reporting threshold | less than reporting threshold |
| Diniconazole | 0.001 | less than reporting threshold | less than reporting threshold | less than reporting threshold | less than reporting threshold | less than reporting threshold | less than reporting threshold |
| Propiconazole | 0.001 | less than reporting threshold | less than reporting threshold | less than reporting threshold | less than reporting threshold | less than reporting threshold | less than reporting threshold |
| Difenoconazole | 0.001 | 0.0023 | less than reporting threshold | 0.0249 | less than reporting threshold | 0.1529 | 0.1647 |
| Teflubenzuron | 0.001 | less than reporting threshold | less than reporting threshold | less than reporting threshold | less than reporting threshold | less than reporting threshold | less than reporting threshold |
| Chlorpyrifos | 0.001 | less than reporting threshold | less than reporting threshold | less than reporting threshold | less than reporting threshold | less than reporting threshold | less than reporting threshold |

Experiments for Mouthfeel Test

1. Experimental subjects: 20 subjects, 10 males and 10 females, aged from 18 to 40.

2. Exclusion criteria: those who has been suffered from oral diseases in the past three months or for a long-term; pregnant women, or women in physiological period; those who have parageusia caused by other situations.

3. Experimental method: each subject was successively administrated with the *Siraitia grosvenori* concentrated solutions obtained in Examples 1 to 3 and Comparative Examples 1 to 3 as the test samples, and each test sample was in a total amount of 10 ml, and consumed within 10 min twice or 3 times. The waiting time after each test sample was consumed was 15 minutes, and the next test sample was consumed after the waiting time. Before the experiment and during the waiting time, the taste of the subjects was cleaned with purified water and inorganic salt biscuits. The mouthfeel of each test sample was evaluated from 11 aspects including characteristic odor, characteristic taste, raw taste, sweetness, bitterness, astringency, duration of sweet aftertaste, duration of bitter aftertaste, duration of astringent aftertaste, characteristic aftertaste and overall consistency. For each indicator, 0 represented the minimum feeling value, 6 represented the maximum feeling value, and each result was represented by the average score.

4. Results

TABLE 3

Effect of different processes on the mouthfeel of *Siraitia grosvenori* concentrated solution

|  | Example 1 | Example 2 | Example 3 | Comparative Example 1 | Comparative Example 2 | Comparative Example 3 |
| --- | --- | --- | --- | --- | --- | --- |
| characteristic odor | 2.8 | 2.5 | 3.0 | 4.8 | 3.5 | 3.8 |
| characteristic taste | 2.1 | 1.9 | 2.6 | 4.6 | 3.8 | 4.2 |
| raw taste | 3.2 | 3.4 | 3.6 | 5.2 | 4.2 | 4.5 |
| sweetness | 5.1 | 5.6 | 5.7 | 3.5 | 4.2 | 4.0 |
| bitterness | 1.5 | 0.8 | 1.4 | 3.5 | 2.8 | 3.0 |
| astringency | 1.4 | 1.2 | 2.2 | 2.4 | 2.6 | 2.3 |
| duration of sweet aftertaste | 4.5 | 4.2 | 4.6 | 5.5 | 4.6 | 4.8 |
| duration of bitter aftertaste | 1.6 | 0.5 | 1.2 | 2.4 | 2.5 | 1.6 |
| duration of astringent aftertaste | 1.0 | 0.4 | 1.5 | 2.2 | 2.8 | 2.6 |
| characteristic aftertaste | 2.8 | 2.0 | 3.0 | 3.5 | 3.8 | 3.9 |
| overall consistency | 4.2 | 4.1 | 4.6 | 5.8 | 5.5 | 5.2 |

CONCLUSION

The test results of the content of mogroside V show that, the contents of mogroside V in the *Siraitia grosvenori* concentrated solutions obtained in Examples 1 to 3 are higher than those obtained in Comparative Examples 1 to 3 by 20.95% on average. Among them, the contents in Example 2 are 37.03%, 30.22%, and 26.06% higher than those in Comparative Examples 1 to 3, respectively. It is shown that the method for separating and purifying mogro side V by subcritical water desorption technology is superior to the prior art.

The detection results of the multiple pesticide residues show that, plural pesticide residue indexes in the *Siraitia grosvenori* concentrated solutions of Examples 1 to 3 are lower than those of Comparative Examples 1 to 3. It is shown that the efficiency of the removal of multiple pesticide residues by subcritical water desorption technology is superior to the prior art.

The results of the mouthfeel test experiment show that, the mouthfeel effects of Examples 1 to 3 are all superior to those of Comparative Examples 1 to 3, wherein the sweetness effect is significantly improved, and the indicators that reduce mouthfeel pleasure such as raw taste, bitterness, astringency are all significantly improved. It is shown that the mouthfeel of the mogroside V-containing *Siraitia grosvenori* concentrated solution separated and purified by subcritical water desorption technology is superior to the prior art.

Although the present invention has been described in detail by general descriptions, specific embodiments, and tests, the present invention can be modified or improved on the basis of the present invention, which will be obvious to a person skilled in the art. Therefore, these modifications or improvements made without departing from the spirit of the present invention all fall within the protection scope of the present invention.

INDUSTRIAL APPLICABILITY

The invention provides a method for separating and purifying mogroside V by subcritical water desorption technology, in which desorption is carried out on the macroporous adsorption resin enriched with mogroside V using water as solvent under a subcritical condition of water, to give an aqueous solution rich in mogro side V. The method provided by the invention improves the content of mogroside V in product, effectively removes bitter impurities and residual pesticides, greatly improves the mouthfeel adaptability of the product, improves the safety and quality of the product, reduces the processing steps and the use of the organic solvents employed in the prior art, and decreases total production costs. The method provided by the invention has good economic value and broad application prospect.

What is claimed is:

1. A method for separating and purifying mogroside V by subcritical water desorption technology, comprising:
   crushing the raw material of *Siraitia grosvenori* fresh fruit or dried fruit, and then extracting with purified water as solvent using a continuous dynamic countercurrent extraction apparatus under the following conditions: a solid-liquid ratio of 50 to 250 g/L, a temperature of 60 to 90° C. a circulation velocity of the purified water of 1,500 to 4,000 L/h, a raw material feeding rate of 500 to 1,500 kg/h, and a time period for extraction of 30 to 180 min, so as to give a water extract of *Siraitia grosvenori;*

(2) centrifuging the water extract of *Siraitia grosvenori* at a rotation speed of 10,000 to 13,000 r/min for 10 to 20 min so as to give a centrifuged liquid;
(3) successively filtering the centrifuged liquid obtained from the centrifuging through a ceramic membrane having a pore size of 50 to 100 μm and a ceramic membrane having a pore size of 5 to 20 μm, so as to give a filtrate; and
(4) absorbing the filtrate on a D101 macroporous adsorption resin with the mass ratio of the macroporous adsorption resin to the raw material of *Siraitia grosvenori* being 1:5 to 1:20, so as to give the macroporous adsorption resin enriched with mogroside V;
(5) subjecting the macroporous adsorption resin enriched with mogroside V to desorption-extraction using 5 to 8 bed volumes (BV) purified water in a subcritical state under a pressure of 8 to 15 MPa and a temperature of 120 to 170° C. at a circulation velocity of 5 to 8 BV/h, to give a *Siraitia grosvenori* aqueous solution: and
(6) concentrating the obtained *Siraitia grosvenori* aqueous solution containing mogroside V through a ceramic membrane with a relative molecular weight cutoff of 150 to 250 Daltons, to give a *Siraitia grosvenori* concentrated solution.

2. The method of claim 1, wherein the desorption-extraction is carried out on the macroporous adsorption resin enriched with mogroside V using 5 BV purified water in a subcritical state under a pressure of 10 MPa and a temperature of 160° C. at a circulation velocity of 5 BV/h, to give a *Siraitia grosvenori* aqueous solution.

3. The method of claim 1, wherein the macroporous adsorption resin enriched with mogroside V is prepared by a method comprising:

(1) crushing the raw material of *Siraitia grosvenori* fresh fruit or dried fruit, and then extracting with purified water as solvent using a continuous dynamic counter-current extraction apparatus under the following conditions: a solid-liquid ratio of 90 g/L, a temperature of 85° C., a circulation velocity of the purified water of 2,500 L/h, a raw material feeding rate of 1,100 kg/h, and a time period for extraction of 120 min, so as to give the water extract of *Siraitia grosvenori*;
(2) centrifuging the water extract of *Siraitia grosvenori* at a rotation speed of 12,000 r/min for 15 min so as to give the centrifuged liquid;
(3) successively filtering the centrifuged liquid through a ceramic membrane having a pore size of 80 μm and a ceramic membrane having a pore size of 10 μm, so as to give the filtrate; and
(4) absorbing the filtrate on the D101 macroporous adsorption resin with the mass ratio of the used macroporous adsorption resin to the raw material of *Siraitia grosvenori* being 1:10, so as to give the macroporous adsorption resin enriched with mogroside V.

4. A method for preparing mogroside V, wherein the mogroside V is prepared by drying the *Siraitia grosvenori* concentrated solution prepared by the method of claim 1.

5. A method for preparing mogroside V, wherein the mogroside V is prepared by drying the *Siraitia grosvenori* concentrated solution prepared by the method of claim 2.

6. A method for preparing mogroside V, wherein the mogroside V is prepared by drying the *Siraitia grosvenori* concentrated solution prepared by the method of claim 3.

* * * * *